(12) United States Patent
Nishiyama et al.

(10) Patent No.: US 6,444,815 B1
(45) Date of Patent: Sep. 3, 2002

(54) METHOD FOR PRODUCING HETEROAROMATIC ALDEHYDES

(75) Inventors: Tetsushi Nishiyama, Osaka (JP); Toru Nakaishi, Sodegaura (JP); Takayuki Shoji, Osaka (JP)

(73) Assignee: Koei Chemical Co., Ltd., Osaka (JP)

( * ) Notice: Subject to any disclaimer, the term of this patent is extended or adjusted under 35 U.S.C. 154(b) by 0 days.

(21) Appl. No.: 09/622,501

(22) PCT Filed: Dec. 13, 1999

(86) PCT No.: PCT/JP99/06983

§ 371 (c)(1),
(2), (4) Date: Aug. 18, 2000

(87) PCT Pub. No.: WO00/37446

PCT Pub. Date: Jun. 29, 2000

(30) Foreign Application Priority Data

Dec. 18, 1998 (JP) .............................................. 10-360412

(51) Int. Cl.[7] .................... C07D 233/20; C07D 233/70; C07D 237/14; C07D 211/40
(52) U.S. Cl. ......................... 544/224; 544/336; 546/314
(58) Field of Search .......................... 546/314; 544/224, 544/336

(56) References Cited

U.S. PATENT DOCUMENTS 5,059,716 A   10/1991   Joentgen et al. ............ 568/435

FOREIGN PATENT DOCUMENTS

| DE | 298 234 A5 | 2/1987 | ........... C07B/33/00 |
| JP | 11-35561 | 2/1999 | ......... C07D/213/48 |

OTHER PUBLICATIONS

HCaplus DN 130:209602, English Abstract JP 11035561. Feb. 1999.*
International Search Report.

* cited by examiner

Primary Examiner—Alan L. Rotman
Assistant Examiner—Rita Desai
(74) Attorney, Agent, or Firm—Sughrue Mion, PLLC

(57) ABSTRACT

There is provided a process for preparing a heteroaromatic aldehyde by catalytic reaction of alkyl-substituted heteroaromatic compound with molecular oxygen in a gaseous phase in the presence of a catalyst, which comprises employing an oxide containing vanadium, phosphorus, aluminium and silicon as a catalyst, and diluting a part or all of the oxide present as a catalyst layer in a reactor with a solid inert to the reaction.

4 Claims, No Drawings

METHOD FOR PRODUCING HETEROAROMATIC ALDEHYDES

This application is a 371 of PCT/JP99/06983 filed Dec. 13, 1999.

TECHNICAL FIELD

The present invention relates to a process for preparing a heteroaromatic aldehyde by catalytic reaction of an alkyl-substituted heteroaromatic compound with molecular oxygen in a gaseous phase. The heteroaromatic aldehyde is a useful compound for various applications such as an raw material for pharmaceutical and agricultural chemicals.

BACKGROUND ART

As a process for preparing a heteroaromatic aldehyde by catalytic reaction of an alkyl-substituted heteroaromatic compound with molecular oxygen, for example German Patent Application DD 298234 Specification discloses a process for preparing 4-pyridinecarbaldehyde by catalytic reaction of 4-methylpyridine with molecular oxygen in a gaseous phase with divanadyl pyrophosphate [$(VO)_2P_2O_7$] as a catalyst.

The present inventors found that, as shown in Comparative Examples, selectivity of 4-pyridinecarbaldehyde was maximum of 60.9% in case of the catalytic reaction of 4-methylpyridine with molecular oxygen in the presence of divanadyl pyrophosphate as the catalyst in a gaseous phase. It was also found that, employing 3-methylpyridine instead of 4-methylpyridine, the selectivity of 3-aldehyde pyridine was also low in case of preparation of 3-pyridinecarbaldehyde by catalytic reaction of 3-methylpyridine with molecular oxygen in a gaseous phase.

Further, according to knowledge of the present inventors, in case of employing divanadyl pyrophosphate as a catalyst, yield of the desired compound (4-pyridinecarbaldehyde, 3-pyridinecarbaldehyde) became extremely low by decreasing an amount of molecular oxygen to increase a concentration of the substrate (4-methylpyridine, 3-methylpyridine) in the reaction materials in order to improve productivity.

Therefore, the processes described above is not satisfactory as the industrial process for preparing a heteroaromatic aldehyde such as pyridinecarbaldehyde, and a process which may prepare a heteroaromatic aldehyde in improved selectivity is desired.

The object of the present invention is to provide a process for solving the problems of the processes in the prior art, namely a process for preparing a heteroaromatic aldehyde by catalytic reaction of an alkyl-substituted heteroaromatic compound with molecular oxygen in a gaseous phase, wherein the heteroaromatic aldehyde is prepared in high selectivity.

DISCLOSURE OF INVENTION

The present inventors have found, as a result of effortful studying in order to solve the above described problems, that the heteroaromatic aldehyde may be prepared from an alkyl-substituted heteroaromatic compound in high selectivity, if the heteroaromatic aldehyde is prepared by catalytic reaction of the alkyl-substituted heteroaromatic compound with molecular oxygen in a gaseous phase, wherein the catalyst is an oxide containing vanadium, phosphorus, aluminium and silicon, and a part or all of the oxide is diluted with a solid inert to the reaction.

Namely, the present invention relates to a process for preparing a heteroaromatic aldehyde by catalytic reaction of an alkyl-substituted heteroaromatic compound with molecular oxygen in a gaseous phase in the presence of a catalyst, which comprises employing an oxide containing vanadium, phosphorus, aluminium and silicon as a catalyst, and diluting a part or all of the oxide present as a catalyst layer in a reactor with a solid inert to the reaction.

BEST MODE FOR CARRYING OUT THE INVENTION

Hereinafter, the present invention is described in detail.

The alkyl-substituted heteroaromatic compound of the present invention is a compound having at least one alkyl group bonding to a carbon atom of a heteroaromatic ring. As the alkyl group, examples are straight or branched alkyl groups having 1 to 4 carbon atoms. Preferably, the compound has one or two nitrogen atoms as a hetero atom of the heteroaromatic ring and at least one of the above alkyl group. More preferably, examples thereof are an alkyl-substituted pyridine, an alkyl-substituted pyrazine and an alkyl-substituted pyrimidine having at least one alkyl group selected from the group consisting of methyl group and ethyl group, concretely the alkyl-substituted pyridine such as 2-methylpyridine, 3-methylpyridine, 4-methylpyridine, 2-ethylpyridine, 3-ethylpyridine, 4-ethylpyridine, 2,3-dimethylpyridine, 2,4-dimethylpyridine, 2,5-dimethylpyridine, 2,6-dimethylpyridine, 3,4-dimethylpyridine, 3,5-dimethylpyridine, 2-methyl-5-ethylpyridine, 2,4,6-trimethylpyridine, 2,3,4-trimethylpyridine, 2,3,5-trimethylpyridine or 2,3,6-trimethylpyridine, the alkyl-substituted pyradine such as methylpyradine, ethylpyradine, 2,3-dimethylpyradine, 2,5-dimethylpyradine, 2,6-dimethylpyradine, 2-methyl-5-ethylpyradine or 2-methyl-6-ethylpyradine, the alkyl-substituted pyrimidine such as 2-methylpyrimidine, 4-methylpyrimidine, 5-methylpyrimidine, 2-ethylpyrimidine, 2,4-dimethylpyrimidine, 2,5-dimethylpyrimidine, 4,5-dimethylpyrimidine or 4,6-dimethylprimidine. The alkyl-substituted heteroaromatic compound may have other groups inert to the reaction in the present invention in addition to the alkyl group, for example at least one group selected from the group consisting of an aryl group, a halogen atom, a hydroxyl group and a cyano group.

According to the present invention, the heteroaromatic aldehydes are obtained by oxidizing at least one alkyl group of the alkyl-substituted heteroaromatic compound to form formyl group (—CHO),.

In the present invention, the oxide containing vanadium, phosphorus, aluminium and silicon is employed as a catalyst. The preferable catalyst is oxide having the formula (I):

$$V_a P_b Al_c Si_d O_e \qquad (I)$$

wherein a, b, c, d and e represent atomic ratios of vanadium, phosphorus, aluminium, silicon and oxygen respectively, b is 0.3 to 3, c is 0 (zero) to 2 excepting 0 (zero), d is 0 (zero) to 6 excepting 0 (zero) when a is 1, and e is decided by atomic valence of oxygen and atomic valences and atomic ratios of the other elements, more preferably oxide having formula (I) wherein b is 0.4 to 2, c is 0.3 to 1.5 and d is 0.1 to 5.5 when a is 1.

The catalyst of the present invention may be prepared by the generally known process for preparing an oxide catalyst. For example, vanadium, phosphorus, aluminium and silicon compounds are heated in a solvent such as water, and stirred.

Then, the obtained mixture is concentrated, dried and calcined in air to obtain an oxide containing vanadium, phosphorus, aluminium and silicon of the catalyst of the present invention.

There is no particular limitation for vanadium, phosphorus, aluminium and silicon compounds employed for the preparation. Examples thereof are a vanadium compound such as ammonium metavanadate, vanadium pentoxide, vanadyl oxalate or vanadyl phosphate; a phosphorus compound such as phosphoric acid, metaphosphoric acid, phosphorous acid or phosphate (for example, ammonium phosphate and the like); an aluminium compound such as aluminium oxide, aluminium hydroxide, aluminium sulfate or aluminium phosphate; a silicon compound such as silicon oxide, silicic acid (such as silica gel or silica sol), silicate (such as sodium silicate, potassium silicate or ammonium silicate) or an alkoxyl silane (such as tetramethoxysilane or tetraethoxysilane).

In the present invention, in order to dilute a part or all of the oxide containing vanadium, phosphorus, aluminium and silicon, which is present as a catalyst layer in a reactor, with a solid inert to the reaction, there are employed the oxide and the solid inert to the reaction. In case that all of the catalyst layer consists only of the oxide containing vanadium, phosphorus, aluminium and silicon, the desired heteroaromatic aldehyde is prepared with low selectivity.

The solid inert to the reaction is a solid which does not act as a catalyst for the reaction of the present invention by itself, and does not promote a side reaction such as decomposition of the alkyl-substituted heteroaromatic compound, and further does not change property thereof under condition of the reaction in the present invention. Any solids as described above can be employed for the present invention. Preferably, it may be a solid conventionally employed as a carrier of a catalyst, examples thereof are silica, alumina, silica-alumina, silicon carbide, titanium oxide, diatomaceous earth, zeolite and the like.

As a process for diluting a part or all of the oxide containing vanadium, phosphorus, aluminium and silicon with the solid inert to the reaction, examples are a method employing a mixture of a part or all of the oxide introduced into the reactor and the solid inert to the reaction, a method employing the oxide carried on the solid inert to the reaction, and the like.

As a process for making the oxide containing vanadium, phosphorus, aluminium and silicon carried on the solid inert to the reaction, examples are a process comprising heating and stirring vanadium, phosphorus, aluminium and silicon compounds and the solid inert to the reaction in a solvent such as water, concentrating the obtained mixture, drying and calcining it under air, a process comprising impregnating an solid inert to the reaction with a solution of vanadium, phosphorus, aluminium and silicon compounds, drying and calcining it, a process comprising mixing an oxide containing vanadium, phosphorus, aluminium and silicon and the solid inert to the reaction optionally by employing a solvent such as water or a process comprising coating the solid inert to the reaction with an oxide containing vanadium, phosphorus, aluminium and silicon. The oxide containing vanadium, phosphorus, aluminium and silicon carried on the solid inert to the reaction, thus obtained, may be further mixed with a solid inert to the reaction and introduced into the reactor.

The oxide containing vanadium, phosphorus, aluminium and silicon (including the oxide carried on the solid inert to the reaction) may be employed for the reaction in the present invention by molding it to the desired shape such as column, cylinder, sphere, grain or fine grain. In preparing the oxide containing vanadium, phosphorus, aluminium and silicon carried on the solid inert to the reaction, the desired oxide in the desired shape is obtained by employing the solid inert to the reaction previously molded to the desired shape.

In diluting a part or all of the oxide containing vanadium, phosphorus, aluminium and silicon with the solid inert to the reaction, a ratio of the oxide to the solid inert to the reaction in the catalyst layer is not particularly limited and may be suitably determined depending on the desired reaction, manner of the reaction, condition of the reaction and the like. Usually, as the ratio of the oxide containing vanadium, phosphorus, aluminium and silicon to the solid inert to the reaction in all of the catalyst layer, the later is determined from 0.1 to 60 parts by weight, preferably 0.5 to 30 parts by weight based on 1 part by weight of the former. The ratio can be easily determined by previously carrying out an experiment in small scale.

The heteroaromatic aldehyde of the present invention may be prepared by the reaction comprising feeding the mixed gas containing the alkyl-substituted heteroaromatic compound and molecular oxygen through the catalyst layer prepared by diluting a part or all of the oxide containing vanadium, phosphorus, aluminium and silicon with the solid inert to the reaction. As a reactor, there may be employed either a fixed bed reactor or a fluidized bed reactor.

The present invention is described in more detail by employing the case employing the fixed bed reactor as an example. A reactor tube is packed with a part of the oxide containing vanadium, phosphorus, aluminium and silicon diluted with the solid inert to the reaction following the remained oxide as it is, or with all of the oxide containing vanadium, phosphorus, aluminium and silicon diluted with the solid inert to the reaction. As the oxide diluted with a solid inert to the reaction, there may be employed at least two oxides having different ratios of the oxide and the solid inert to the reaction. Preferably, the packing is carried out in such a manner that a ratio of the employed oxide containing vanadium, phosphorus, aluminium and silicon and the inactive solid for the reaction is introduced by increasing a concentration of the oxide from inlet side of the raw material mixed gas to outlet side of the gas produced by the reaction, or in such a manner that the concentration of the oxide becomes almost uniform in all of the catalyst layer.

A ratio of the employed alkyl-substituted heteroaromatic compound to molecular oxygen is usually 0.4 to 5.0 moles, preferably 0.4 to 3.0 moles, more preferably 1.1 to 2.1 moles of the molecular oxygen based on 1 mole of the alkyl-substituted heteroaromatic compound. As the molecular oxygen, air may be usually employed, but pure oxygen or the mixture thereof with air may be employed. In the course of the reaction, the mixed gas containing the alkyl-substituted heteroaromatic compound and molecular oxygen may be diluted with the inert gas such as nitrogen or water vapor, particularly in case of the reaction employing the fixed bed reactor, the inert gas is preferably employed to inhibit forming explosive mixture by the mixed gas. Preferable inert gas is water vapor. In case of employing the inert gas, an amount thereof is usually 15 to 50 moles, preferably 20 to 30 moles based on 1 mole of the alkyl-substituted heteroaromatic compound.

The catalyst layer in the reactor tube is usually heated from 250 to 500° C., preferably from 280 to 450° C., and the mixed gas containing the alkyl-substituted heteroaromatic compound, molecular oxygen and optionally the inert gas in the ratio is fed through the catalyst layer in a space-velocity (hereinafter referred to as SV) of usually 700 to 11000 hr$^{-1}$, preferably 1500 to 5000 hr$^{-1}$ to prepare the heteroaromatic aldehyde in a high yield. The reaction can be carried out under normal pressure, reduced pressure or elevated pressure.

The reacted gas obtained by the reaction in the present invention is cooled as it is and/or bubbled into a suitable solvent for condensation of the heteroaromatic aldehyde and/or dissolving it in the solvent, then concentrated, extracted and evaporated to isolate the heteroaromatic aldehyde from the condensate and/or the solution.

Hereinafter, the present invention is further concretely explained by Examples, but not limited thereto.

Conversion, yield and selectivity were calculated according to the following definitions.

Conversion (%)=Reacted Methylpyridine (mole)/Supplied Methylpyridine for Reaction (mole)×100

Yield (%)=Produced Pyridinecarbaldehyde (mole)/Supplied Methylpyridine for Reaction (mole)×100

Selectivity (%)=Produced Pyridinecarbaldehyde (mole)/Reacted Methylpyridine (mole)×100

EXAMPLE 1

Preparation of a Catalyst

There were mixed with 500 g of ion-exchanged water and 45.6 g of 85% phosphoric acid with stirring and the mixture was heated to 90° C. To the aqueous phosphoric acid solution were added 30.0 g of vanadium pentoxide, 84.1 g of 10% by weight of alumina sol and 19.8 g of silica gel. The obtained mixture was stirred at 90° C. for 20 minutes and concentrated. Then the concentrate was dried at 200° C. overnight and calcined under air at 640° C. for 4 hours. Thus the oxide having $V_1P_{1.2}Al_{0.5}Si_{1.0}$ in an atomic ratio without oxygen was obtained.

Preparation of 4-pyridinecarbaldehyde 4-pyridinecarbaldehyde was prepared with the oxide as a catalyst. Grain size of the oxide having $V_1P_{1.2}Al_{0.5}Si_{1.0}$ in anatomic ratio without oxygen was uniformed to from 1.0 to 1.7 mm (10 to 16 mesh). A Pyrex reactor tube having 18 mm of an inside diameter was packed with 5 ml of oxide having the grain size uniformed, and further packed with 5 ml of the oxide having the uniformed grain size diluted with 5 ml of silicon carbide having the same grain size thereon. A packing ratio in the reactor tube of the oxide to silicon carbide (ratio by weight) was 1 to 0.62. The catalyst-packed portion in the reactor tube was heated to 350° C. A mixed gas containing 4-methylpyridine, water and air (mixing molar ratio was 4-methylpyridine:water:air=1:30:10) was feeded from upper side of the reactor tube at SV=1940 hr$^{-1}$ to carry out the reaction. Reacted gas exhausted from the reactor tube was bubbled into 100 ml of water for 10 minutes to collect the reaction product in the reacted gas. The collecting liquid obtained was analyzed by gas chromatography. The results are shown in Table 1.

EXAMPLE 2

Preparation of a Catalyst

A catalyst was prepared in the same manner as in Example 1 to obtain a oxide having $V_1P_{1.8}Al_{1.0}Si_{1.0}$ in atomic ratio without oxygen, except that amounts of 85% phosphoric acid and silica gel were changed to 34.2 g and 9.9 g, respectively.

Preparation of 4-pyridinecarbaldehyde 4-pyridinecarbaldehyde was prepared in the same manner as in Example 1, except that the oxide having $V_1P_{1.2}Al_{0.5}Si_{1.0}$ in atomic ratio but oxygen was replaced by the oxide having $V_1P_{1.8}Al_{1.0}Si_{1.0}$ in atomic ratio without oxygen obtained as described above and a heating temperature of the catalyst-packed part of the reaction tube was changed to 360° C. A ratio of the oxide to silicon carbide (ratio by weight) was 1 to 0.66. The results are shown in Table 1.

EXAMPLE 3

Preparation of a Catalyst

A catalyst was prepared in the same manner as in Example 1 to obtain an oxide having $V_1P_{0.5}Al_{0.5}Si_{1.0}$ in atomic ratio but oxygen, except that an amount of 85% phosphoric acid was changed to 19 g.

Preparation of 4-pyridinecarbaldehyde 4-pyridinecarbaldehyde was prepared in the manner of Example 1, except that the oxide having $V_1P_{1.2}Al_{0.5}Si_{1.0}$ in atomic ratio but oxygen was replaced by the oxide having $V_1P_{0.5}Al_{0.5}Si_{1.0}$ in atomic ratio but oxygen obtained as described above and a heating temperature of the catalyst-packed portion of the reaction tube was changed to 300° C. The ratio of the oxide to silicon carbide (ratio by weight) was 1 to 0.86. The results are shown in Table 1.

Comparative Example 1

Preparation of a Catalyst

Divanadyl pyrophosphate was prepared by the following process based on the description of Japanese Examined Patent Publication No. 1981-45815.

There were mixed 450.0 g of ion-exchanged water, 34.6 g of 85% phosphoric acid and 20.9 g of hydroxyl amine hydrochloride were mixed with stirring, heated to 80° C. To the mixture was added 300.0 g of ion-exchanged water, then 27.3 g of vanadium pentoxide to react. Vanadium pentoxide was slowly added, since the reaction is accompanied with foaming. After adding vanadium pentoxide, the mixture was concentrated to obtain a cerulean slurry. The obtained slurry was dried at 170° C. over night, crashed, washed by stirring it in ion-exchanged water and filtered. The obtained solid was dried at 120° C. over night, introduced in Pyrex reactor tube having 22 mm φ and calcined under nitrogen atmosphere at 500° C. for 6 hours. Thus obtained product was analyzed by X-ray diffraction and Identified as divanadyl pyrophosphate [$(VO)_2P_2O_7$].

Preparation of 4-pyridinecarbaldehyde 4-pyridinecarbaldehyde was prepared in the same manner as in Example 1, except that an oxide having $V_1P_{1.2}Al_{0.5}Si_{1.0}$ in atomic ratio without oxygen was replaced by 10 ml of divanadyl pyrophosphate obtained as described above as it is and heating temperatures of the catalyst-packed portion of the reaction tube were changed to those shown in Table 1. The results are shown in Table 1.

Comparative Example 2

Preparation of 4-pyridinecarbaldehyde 4-pyridinecarbaldehyde was prepared in the same manner as in Example 1, except that an oxide having $V_1P_{1.2}Al_{0.5}Si_{1.0}$ in atomic ratio without oxygen was replaced by divanadyl pyrophosphate obtained as described above and heating temperatures of the catalyst-packed portion of the reaction tube were changed to those shown in Table 1. The results are shown in Table 1.

Comparative Example 3

Preparation of 4-pyridinecarbaldehyde 4-pyridinecarbaldehyde was prepared in the same manner as in Example 1, except that silicon carbide was not employed, the amount of the oxide (grain size; 1.0 to 1.7 mm) having $V_1P_{1.2}Al_{0.5}Si_{1.0}$ in atomic ratio without oxygen was changed to 10 ml and heating temperatures of the catalyst-packed portion of the reaction tube were changed to those shown in Table 1. The results are shown in Table 1.

without oxygen obtained as described above, 4-methylpyridine was replaced by 3-methylpyridine and a heating temperature of the catalyst- packed portion of the reaction tube was changed to 380° C. The ratio of the oxide to silicon carbide (ratio by weight) was 1 to 1.3. As results, conversion of 3-methylpyridine was 47.1%, and yield and selectivity of 3-pyridinecarbaldehyde was 17.3% and 36.7%, respectively.

Comparative Example 4

Preparation of 3-pyridinecarbaldehyde 3-pyridinecarbaldehyde was prepared in the same manner as in Example 5, except that the reactor tube packed with the

TABLE 1

| | Catalyst | Temp. ° C. | 4-Methylpyridine Conversion(%) | 4-pyridine Yield(%) | carbaldehyde Selectivity(%) |
|---|---|---|---|---|---|
| Example No. | | | | | |
| 1 | $V_1P_{1.2}Al_{0.5}Si_{1.0}$ Diluted | 350 | 78.2 | 69.4 | 88.8 |
| 2 | $V_1P_{1.8}Al_{1.0}Si_{1.0}$ Diluted | 360 | 84.4 | 60.0 | 71.0 |
| 3 | $V_1P_{0.5}Al_{0.5}Si_{1.0}$ Diluted | 300 | 76.7 | 54.4 | 71.0 |
| Comparative Example | | | | | |
| 1 | $(VO)_2P_2O_7$ Not Diluted | 340 | 67.1 | 39.6 | 59.0 |
| | | 350 | 86.7 | 52.9 | 60.9 |
| | | 360 | 97.1 | 46.1 | 47.5 |
| 2 | $(VO)_2P_2O_7$ Diluted | 320 | 57.4 | 25.1 | 43.7 |
| | | 330 | 73.4 | 43.0 | 58.6 |
| | | 340 | 87.6 | 41.8 | 47.8 |
| 3 | $V_1P_{1.2}Al_{0.5}Si_{1.0}$ Not Diluted | 270 | 65.6 | 26.9 | 41.0 |
| | | 280 | 81.2 | 35.5 | 47.7 |
| | | 285 | 93.6 | 40.5 | 43.2 |
| | | 290 | 100 | 29.1 | 29.1 |

EXAMPLE 4

Preparation of 4-pyridinecarbaldehyde 4-pyridinecarbaldehyde was prepared in the same manner as in Example 1, except that the catalyst layer was replaced by 10 ml of 1 part by weight of the oxide having $V_1P_{1.8}Al_{1.0}Si_{1.0}$ in atomic ratio without oxygen diluted with 4 parts by weight of fused alumina and a heating temperature of the catalyst-packed portion of the reaction tube was changed to 380° C. As results, the conversion of 4-methylpyridine was 87.4%, and the yield and the selectivity of 4-pyridinecarbaldehyde was 64.3% and 73.5%, respectively.

EXAMPLE 5

Preparation of a Catalyst

A catalyst was prepared in the same manner as in Example 1 to obtain a oxide having $V_1P_{1.2}Al_{0.5}Si_{5.0}$ in atomic ratio without oxygen, except that the amount of silica gel was changed to 99.0 g.

Preparation 3-pyridinecarbaldehyde 3-pyridinecarbaldehyde was prepared in the same manner as in Example 1, except that the oxide having $V_1P_{1.2}Al_{0.5}Si_{1.0}$ in atomic ratio without oxygen was replaced by the oxide having $V_1P_{1.2}Al_{0.5}Si_{5.0}$ in atomic ratio oxide having $V_1P_{1.2}Al_{0.5}Si_{5.0}$ in atomic ratio without oxygen was replaced by the reactor tube packed with divanadyl pyrophosphate in Comparative Example 1 and a heating temperature of the catalyst-packed portion of the reaction tube was changed to 390° C. As results, conversion of 3-methylpyridine was 56.2%, and yield and selectivity of 3-pyridinecarbaldehyde was 16.6% and 29.5%, respectively.

EXAMPLE 6

Preparation of 3-pyridinecarbaldehyde 3-pyridinecarbaldehyde was prepared in the same manner as in Example 4, except that 4-methylpyridine was replaced by 3-methylpyridine and a heating temperature of the catalyst-packed portion of the reaction tube was changed to 430° C. As results, conversion of 3-methylpyridine was 57.7%, and yield and selectivity of 3-pyridinecarbaldehyde was 19.9% and 34.6%, respectively.

EXAMPLE 7

Preparation of 2-pyridinecarbaldehyde 2-pyridinecarbaldehyde was prepared in the same manner as in Example 4, except that 4-methylpyridine was replaced by 2-methylpyridine, the mixed gas was fed from upper side of the reactor tube at SV=3550 hr$^{-1}$ and a heating temperature of the catalyst-packed portion of the reaction tube was changed to 430° C. As results, conversion of 2-methylpyridine was 50.7%, and yield and selectivity of 2-pyridinecarbaldehyde was 39.2% and 77.3%, respectively.

Comparative Example 5

Preparation of 2-pyridinecarbaldehyde 2-pyridinecarbaldehyde was prepared in the same manner as in Example 7, except that the reactor tube was replaced by a reactor tube packed with divanadyl pyrophosphate in Comparative Example 1 and a heating temperature of the catalyst-packed portion of the reaction tube was changed to 390° C. As results, conversion of 2-methylpyridine was 48.2%, and yield of 2-pyridinecarbaldehyde was 12.7% (the selectivity 26.3%). Pyridine was also prepared at 12.9% in yield. In case of employing the oxide (divanadyl pyrophosphate) containing vanadium and phosphorus and not containing aluminium and silicon as the catalyst, by increase of the amount of employed molecular oxygen, the yield of the heteroaromatic aldehyde may be increased, but by decrease of the amount of employed molecular oxygen, the yield is extremely decreased. On the other hand, according to the present invention, yield of the heteroaromatic aldehyde is high by employing the oxide containing vanadium, phosphorus, aluminium and silicon as catalyst, even when an amount of employed molecular oxygen is decreased.

INDUSTRIAL APPLICABILITY

The present invention is useful for preparing a heteroaromatic aldehyde by employing an alkyl-substituted heteroaromatic compound as a starting material. The heteroaromatic aldehyde is useful compound as raw material for pharmaceutical and agricultural chemicals and the like.

What is claimed is:

1. A process for preparing a heteroaromatic aldehyde by catalytic reaction of an alkyl-substituted heteroaromatic compound with molecular oxygen in a gaseous phase in the presence of a catalyst, which comprises employing an oxide containing vanadium, phosphorus, aluminum and silicon as a catalyst, and diluting a part or all of the oxide present as a catalyst layer in a reactor with a solid inert to the reaction, wherein the alkyl-substituted heteroaromatic compound is at least one selected from the group consisting of an alkyl-substituted pyridine, an alkyl-substituted pyrazine and an alkyl-substituted pyrimidine.

2. A process according to claim 1 wherein the catalyst is an oxide represented by the formula (I):

$$V_a P_b Al_c Si_d O_e \qquad (I)$$

wherein a, b, c, d and e represent atomic ratios of vanadium, phosphorus, aluminium, silicon and oxygen, respectively, b is 0.3 to 3, c is 0 (zero) to 2 excepting 0 (zero), d is 0 (zero) to 6 excepting 0 (zero) when a is 1, and e is decided by an atomic valence of oxygen and an atomic valence and an atomic ratio of the other elements.

3. A process according to claim 1, wherein the solid inert to the reaction is at least one selected from the group consisting of silica, alumina, silica-alumina, silicon carbide, diatomaceous earth and zeolite.

4. A process according to claim 1 wherein an ratio of the alkyl-substituted heteroaromatic compound to the molecular oxygen is from 0.4 to 3.0 moles of the molecular oxygen based on 1 mole of the alkyl-substituted heteroaromatic compound.

* * * * *